US010509976B2

(12) United States Patent
Lewis et al.

(10) Patent No.: US 10,509,976 B2
(45) Date of Patent: Dec. 17, 2019

(54) HETEROGENEOUS FLUID SAMPLE CHARACTERIZATION

(71) Applicant: Malvern Panalytical Limited, Worcestershire (GB)

(72) Inventors: E. Neil Lewis, Olney, MD (US); John McCaffrey, Columbia, MD (US); Ken Haber, Frederick, MD (US); Peter Bennett, Columbia, MD (US); Gerald Sando, Columbia, MD (US); Tomasz Sadowski, Warsaw (PL)

(73) Assignee: Malvern Panalytical Limited, Malvern, Worcestershire (GB)

( * ) Notice: Subject to any disclaimer, the term of this patent is extended or adjusted under 35 U.S.C. 154(b) by 131 days.

(21) Appl. No.: 14/410,513

(22) PCT Filed: Jun. 21, 2013

(86) PCT No.: PCT/GB2013/051642

§ 371 (c)(1),
(2) Date: Dec. 22, 2014

(87) PCT Pub. No.: WO2013/190327

PCT Pub. Date: Dec. 27, 2013

(65) Prior Publication Data

US 2015/0338334 A1 Nov. 26, 2015

Related U.S. Application Data

(63) Continuation-in-part of application No. 13/841,721, filed on Mar. 15, 2013, now abandoned.

(Continued)

(51) Int. Cl.
*G06K 9/00* (2006.01)
*G06K 9/20* (2006.01)

(Continued)

(52) U.S. Cl.
CPC ....... *G06K 9/2027* (2013.01); *G01N 15/1429* (2013.01); *G01N 15/1459* (2013.01);

(Continued)

(58) Field of Classification Search
None
See application file for complete search history.

(56) References Cited

U.S. PATENT DOCUMENTS 5,086,643 A * 2/1992 Marek ................ G01N 15/0826 73/38
5,825,477 A * 10/1998 Furuie ................ G01N 15/0227 356/335

(Continued)

FOREIGN PATENT DOCUMENTS

| | | |
|---|---|---|
| CN | 1086313 | 5/1994 |
| CN | 1800820 | 7/2006 |

(Continued)

OTHER PUBLICATIONS

Zheng, G. et al. (2010). "Sub-pixel resolving optofluidic microscope for on-chip cell imaging," *The Royal Society of Chemistry* 10: 3125-3129.

(Continued)

*Primary Examiner* — Randolph I Chu
(74) *Attorney, Agent, or Firm* — Morrison & Foerster LLP

(57) ABSTRACT

The disclosure relates to methods and device for detecting properties of heterogeneous samples, including detecting properties of particles or fluid droplets in industrial processes. A probe may be inserted into a first of multiple heterogeneous fluid samples. A portion of the first sample may be drawn into the probe and past a two-dimensional array detector. The portion of the first sample may be illuminated as it is drawn past the array detector and an (Continued)

134 image of the portion of the first sample may be acquired. The probe may be inserted into a second of multiple heterogeneous fluid samples. A portion of the second sample may be drawn into the probe and past a two-dimensional array detector. The portion of the second sample may be illuminated as it is drawn past the array detector and an image of the portion of the second sample may be acquired.

16 Claims, 11 Drawing Sheets

Related U.S. Application Data

(60) Provisional application No. 61/835,409, filed on Jun. 14, 2013, provisional application No. 61/679,662, filed on Aug. 3, 2012, provisional application No. 61/663,527, filed on Jun. 22, 2012.

(51) Int. Cl.
*G01N 15/14* (2006.01)
*G01N 15/10* (2006.01)

(52) U.S. Cl.
CPC ..... *G01N 15/1463* (2013.01); *G06K 9/00134* (2013.01); *G06K 9/00147* (2013.01); *G01N 2015/1043* (2013.01); *G01N 2015/1402* (2013.01); *G01N 2015/1493* (2013.01); *G01N 2015/1497* (2013.01)

(56) References Cited

U.S. PATENT DOCUMENTS 5,991,470 A 11/1999 Swithers et al.
6,002,476 A 12/1999 Treado
6,037,772 A 3/2000 Karczmar et al.
6,060,202 A * 5/2000 Ogawa .................. G03G 9/097 399/225
6,067,154 A 5/2000 Hossain et al.
6,200,820 B1 * 3/2001 Hansen .................. G01N 15/14 435/6.1
6,288,782 B1 9/2001 Worster et al.
6,545,755 B1 4/2003 Ishihama et al.
7,061,606 B2 6/2006 Treado et al.
7,532,320 B2 5/2009 Neiss et al.
7,595,878 B2 9/2009 Nelson et al.
8,111,395 B2 2/2012 Lewis
2003/0016857 A1 1/2003 Wang et al.
2003/0124611 A1 7/2003 Schwartz
2004/0132383 A1 * 7/2004 Langford ................ B24C 1/045 451/38
2004/0235181 A1 11/2004 Arnold et al.
2005/0179899 A1 8/2005 Palti-Wasserman et al.
2005/0248761 A1 * 11/2005 Nieuwenhuis ..... G01N 15/0227 356/335
2005/0277816 A1 12/2005 Maier et al.
2006/0063989 A1 3/2006 Hogan
2006/0121442 A1 6/2006 Perraut et al.
2006/0170916 A1 8/2006 Voigt et al.
2007/0127022 A1 6/2007 Cohen et al.
2008/0084553 A1 4/2008 Neiss et al.
2008/0100840 A1 5/2008 Oma et al.
2008/0317325 A1 12/2008 Ortyn et al.
2009/0226031 A1 9/2009 Izuka
2010/0013938 A1 1/2010 Fukuda et al.
2010/0154529 A1 * 6/2010 Terabayashi ............ E21B 49/10 73/152.27
2010/0178666 A1 7/2010 Leshansky et al.
2010/0252118 A1 10/2010 Fraden et al.
2011/0096157 A1 4/2011 Fine et al.
2012/0034623 A1 * 2/2012 Hulsken ............... G01N 1/4005 435/7.2
2012/0045103 A1 2/2012 Salsman et al.
2012/0250027 A1 * 10/2012 Zheng .................... B82Y 20/00 356/491
2012/0292233 A1 11/2012 Toner et al.
2013/0120556 A1 * 5/2013 Dorris ...................... G06K 9/78 348/92
2013/0229663 A1 * 9/2013 Yang .................... A61B 5/0062 356/497
2014/0002662 A1 * 1/2014 Lewis ................ G01N 15/0612 348/159
2014/0071452 A1 * 3/2014 Fleischer ........... G01N 15/1434 356/436
2014/0113277 A1 * 4/2014 Thomas ............... G01N 29/032 435/5
2014/0255967 A1 * 9/2014 Dancu ................ G01N 33/5005 435/29
2015/0362421 A1 * 12/2015 Lewis ................ G01N 15/1463 356/343

FOREIGN PATENT DOCUMENTS

| | | |
|---|---|---|
| CN | 101438143 | 5/2009 |
| CN | 101772697 | 7/2010 |
| CN | 102494869 | 6/2012 |
| EP | 0614077 | 9/1994 |
| JP | 62-86990 | 4/1987 |
| JP | 63-148147 | 6/1988 |
| JP | 2-36334 | 2/1990 |
| JP | 2000-146817 | 5/2000 |
| JP | 2003-21590 | 1/2003 |
| JP | 2003-84005 | 3/2003 |
| JP | 2004-12373 | 1/2004 |
| JP | 2004-532988 | 10/2004 |
| JP | 2006-238802 | 9/2006 |
| JP | 2007-58354 | 3/2007 |
| JP | 2009-236828 | 10/2009 |
| JP | 4623516 | 11/2010 |
| JP | 2011-80883 | 4/2011 |
| WO | WO-92/22880 | 12/1992 |
| WO | WO-01/22060 | 3/2001 |
| WO | WO-2008/120321 | 10/2008 |
| WO | WO-2011/006525 | 1/2011 |
| WO | WO-2012/082776 | 6/2012 |

OTHER PUBLICATIONS

Valet et al., U.S. Appl. No. 10/088,008, filed Aug. 15, 2000; 14 pages.
International Search Report dated Dec. 6, 2013, directed to International Application No. PCT/GB2013/051641, 4 pages.
Zhang, X. et al. (2011). "Lensless imaging for simultaneous microfluidic sperm monitoring and sorting," *The Royal Society of Chemistry* 11: 2535-2540.
Ozcan, A. et al. (2008). "Ultra wide-field lens-free monitoring of cells on-chip," *The Royal Society of Chemistry* 8: 98-106.
International Search Report dated Jun. 12, 2013, directed towards International Application No. PCT/GB2013/051642, 5 pages.
Lewis, U.S. Office Action dated Apr. 2, 2009, directed to U.S. Appl. No. 12/006,677; 12 pages.
Lewis, U.S. Office Action dated Feb. 1, 2010, directed to U.S. Appl. No. 12/006,677; 11 pages.
Lewis, U.S. Office Action dated Dec. 22, 2010, directed to U.S. Appl. No. 12/006,677; 9 pages.
O'Brien, D. (n.d.). Cassini Lossy Compression Software Tests. Retrieved from Image Entropy: http://www.astro.cornell.edu/research/projects/compression/entropy.html). 1 page.
Flat field and dark frame correction (Oct. 8, 2007). Retrieved Feb. 24, 2017, from http://www.cfht.hawaii.edu/~baril/Pyxis/Help/flatdarkfield.html. 2 pages.
Lewis, U.S. Office Action dated Jul. 27, 2016, directed to U.S. Appl. No. 14/408,833; 23 pages.
Lewis U.S. Office Action dated Mar. 3, 2017, directed to U.S. Appl. No. 14/408,833; 23 pages.
Japanese Notice of Reasons for Rejection dated Jun. 6, 2017, directed to Japanese Patent Application No. 2015-517859; 10 pages.
Japanese Notice of Reasons for Rejection dated Jun. 6, 2017,

(56) References Cited

OTHER PUBLICATIONS directed to Japanese Patent Application No. 2015-517860, 5 pages.
Notice of Reasons for Rejection dated Nov. 27, 2018, directed to JP Application No. 2015-517860; 8 pages.
Decision of Refusal dated Dec. 26, 2017, directed to Japanese Application No. 2015-517859; 32 pages.
First Office Action dated Mar. 4, 2016, directed to Chinese Application No. 201380044016.6; 18 pages.
First Office Action dated May 30, 2016, directed to Chinese Application No. 201380033125.8; 19 pages.
Fourth Office Action dated Feb. 8, 2018, directed to Chinese Application No. 201380044016.6; 7 pages.
Notification of Reasons for Refusal dated Feb. 27, 2018, directed to Japanese Application No. 2015-517860; 35 pages.
Second Office Action dated Nov. 23, 2016, directed to Chinese Application No. 201380033125.8; 18 pages.
Second Office Action dated Sep. 20, 2016, directed to Chinese Application No. 201380044016.6; 28 pages.
Third Office Action dated Mar. 7, 2017, directed to Chinese Application No. 201380044016.6; 31 pages.
Third Office Action dated May 9, 2017, directed to Chinese Application No. 201380033125.8; 19 pages.
Third Party Submission dated Feb. 6, 2019, directed to JP Application No. 2015-517860; 10 pages.

* cited by examiner

90

96

HETEROGENEOUS FLUID SAMPLE CHARACTERIZATION

REFERENCE TO RELATED APPLICATIONS

This application is a national stage application under 35 USC 371 of International Application No. PCT/GB2013/051642, filed Jun. 21, 2013, which claims the priority of Provisional Application No. 61/663,527, filed Jun. 22, 2012, Provisional Application No. 61/679,662, filed Aug. 3, 2012, U.S. application Ser. No. 13/841,721, filed Mar. 15, 2013, and Provisional Application No. 61/835,409, filed Jun. 14, 2013, the entire contents of which are incorporated herein by reference.

FIELD OF THE INVENTION

This invention relates to methods and apparatus for detecting properties of heterogeneous fluid samples, including detecting properties of particles or fluid droplets, which may be used for example in industrial processes.

BACKGROUND OF THE INVENTION

Lensless microfluidic detection techniques have been proposed to acquire microscopic images of samples such as biological materials and cells. They operate by acquiring images of suspended samples in close proximity to a high-resolution imaging detector. Their small size has resulted in their use being proposed in a variety of life science applications, including microscopes, smart petri dishes, and point-of-care diagnostic systems.

SUMMARY OF THE INVENTION

In one general aspect, the invention features a particle characterization method that includes suspending particles in a fluid, causing them to flow past a two-dimensional array detector, and illuminating them as they do so. The method also includes acquiring images of the particles as they flow past the two-dimensional array detector in the fluid, and applying a particle characterization function to the images for at least some of the suspended particles.

In preferred embodiments the step of applying a particle characterization function can categorize the particles according to at least one morphological characteristic. The step of applying a particle characterization function can categorize the particles according to their shapes. The step of applying a particle characterization function can categorize the particles according to their sizes. The step of applying a particle characterization function can categorize the particles statistically. The step of illuminating can include a step of strobing a source for a plurality of short acquisition periods with the step of acquiring the images during the plurality of short acquisition periods. The method can further include the step of displaying the images of the particles in a sorted thumbnail view. The steps of suspending, causing, acquiring, and applying can be carried out as part of a molecular microbiological method. The steps of suspending, causing, acquiring, and applying can be part of a manufacturing process quality assurance cycle. The steps of suspending, causing, acquiring, and applying can be part of a manufacturing process quality control evaluation. The steps of suspending, causing, acquiring, and applying can be applied to evaluate a dispersion step. The steps of suspending, causing, acquiring, and applying can be applied to pharmaceutical composition particles. The step of applying a particle characterization function can apply a contaminant detection function. The step of applying a particle characterization function can apply a counterfeit detection function. The method can further include the step of performing an additional particle characterization operation while the particles are suspended in the same fluid. The further particle characterization operation can include a laser diffraction step. The further particle characterization operation can take place in parallel with the steps of causing, acquiring, and applying. The further particle characterization operation can take place in series with the steps of causing, acquiring, and applying. The method can further include the step of extracting images of individual particles from image data received in the step of acquiring and transferring these extracted images through a communication channel to a user computer. The step of causing the suspended particles to flow past a two-dimensional array detector can cause them to flow along a single flow path that has a profile that includes a detector flow region and a pair of bypass channels. The step of causing the suspended particles to flow past a two-dimensional array detector can cause them to flow along a path with substantially no zero-flow regions. The step of causing the suspended particles to flow past a two-dimensional array detector can cause them to flow at a flow rate of at least one liter per minute.

The method can further include the step of applying a statistical function to image data from the two-dimensional array detector to gage heterogeneity. The statistical function may involve calculating a measure of entropy in the plurality of acquire images. The measure of entropy may be calculated from a sum of probabilities of pixel values or differences between adjacent pixel values in each acquired images being a given value.

The fluid can be a liquid. The particles may be individual particles or agglomerates of particles suspended in a fluid, which may be a liquid or a gas. The particles may alternatively be droplets of a first liquid dispersed in a second liquid or gas, the first and second fluids being immiscible. The particles may be solid, porous or hollow. The particles may be biological particles such as cells, proteins or virus particles.

In another general aspect, the invention features a particle characterization instrument that includes a two-dimensional array detector, channel walls mounted to the detector for defining a channel to hold a fluid containing a sample in contact with the two-dimensional detector, a driver to move the fluid through the channel, an imaging illumination source positioned to illuminate particles in the fluid while it is in contact with the two-dimensional detector, and a coherent scattering illumination source positioned to illuminate particles in the fluid.

In preferred embodiments the coherent scattering illumination source can be positioned to interact with the fluid while it is in contact with the two-dimensional detector with the two-dimensional detector being positioned to both detect light from particles illuminated by the imaging illumination detector and to detect light scattered by particles in the fluid illuminated by the coherent scattering illumination source. The instrument can further include a scattering detector positioned to receive light scattered by particles in the fluid illuminated by the coherent scattering illumination source.

In a further general aspect, the invention features a particle characterization method that includes suspending particles in a fluid, causing the suspended particles to flow in the fluid past a two-dimensional array detector, and acquiring a plurality of calibration images of the particles as they flow past the two-dimensional array detector in the fluid, illuminating the suspended particles as they flow past the two-dimensional array detector in the fluid, acquiring a plurality of sample images of the particles as they flow past the two-dimensional array detector in the fluid, and correcting the sample images of the particles using the calibration images. The calibration images are preferably acquired prior to acquiring the sample images, although in some cases may be acquired after the sample images are acquired.

In preferred embodiments the step of correcting can perform a flat-field correction. The step of acquiring a plurality of calibration images of the particles can acquire illuminated images and dark images. The method can further include the step of averaging the acquired calibration images to reduce the effect of the suspended particles in a result of the step of averaging. The method can further include the step of discarding pixels exceeding a predetermined threshold in the calibration images before the step of averaging.

In another general aspect, the invention features a particle characterization instrument that includes means for causing the suspended particles to flow past a two-dimensional array detector, means for illuminating the suspended particles as they flow past the two-dimensional array detector in the fluid, means for acquiring a plurality of images of the particles as they flow past the two-dimensional array detector in the fluid, and means for applying a particle characterization function to results from the means for acquiring for at least some of the suspended particles.

In a further general aspect, the invention features a particle characterization method that includes suspending particles in a fluid, causing a first subset of the suspended particles to flow past a first two-dimensional array detector, illuminating the first subset of suspended particles as they flow past the first two-dimensional array detector in the fluid, acquiring a plurality of images of the first subset of particles as they flow past the first two-dimensional array detector in the fluid, causing a second subset of the suspended particles to flow past a second two-dimensional array detector, illuminating the second subset of suspended particles as they flow past the second two-dimensional array detector in the fluid, and acquiring a plurality of images of the second subset of particles as they flow past the second two-dimensional array detector in the fluid.

In preferred embodiments, the step of causing a first subset of the suspended particles to flow past the first two-dimensional array detector and the step of causing a second subset of the suspended particles to flow past the second two-dimensional array detector can be performed in series. The step of causing a first subset of the suspended particles to flow past the first two-dimensional array detector and the step of causing a second subset of the suspended particles to flow past the second two-dimensional array detector can be performed in parallel. The method can further include the step of combining information from the images from the first and second two-dimensional array detectors. The step of causing a first subset of the suspended particles to flow past the first two-dimensional array detector and the step of causing a second subset of the suspended particles to flow past the second two-dimensional array detector can together cause the average size of particles that flow over the second array to be larger than the average size of particles that flow over the first array. The step of causing a first subset of the suspended particles to flow past the first two-dimensional array detector can cause the first subset of particles to flow through a first channel that has a first depth in front of the first detector, and the step of causing a second subset of the suspended particles to flow past the second two-dimensional array detector can cause the second subset of particles to flow through a second channel that has a second depth in front of the second detector, and wherein the first depth is deeper than the second depth. The step of causing a first subset of the suspended particles to flow past the first two-dimensional array detector can cause the first subset of particles to flow through a first compound channel that includes an imaging subchannel and one or more bypass subchannels that are larger than the imaging channel, with the step of causing a second subset of the suspended particles to flow past the second two-dimensional array detector causing the second subset of particles to flow through a second compound channel that includes an imaging subchannel and one or more bypass subchannels that are larger than the imaging channel. The step of causing a first subset of the suspended particles to flow past the first two-dimensional array detector can cause the first subset of particles to flow through a first compound channel that includes an imaging subchannel and one or more bypass subchannels that are larger than the imaging channel, with the step of causing a second subset of the suspended particles to flow past the second two-dimensional array detector causing the second subset of particles to flow through a second compound channel that includes an imaging subchannel and one or more bypass subchannels that are larger than the imaging channel. The method can further include the step of causing one or more further subsets of the suspended particles to flow past one or more further two-dimensional array detectors, illuminating the further subsets of suspended particles as they flow past the further two-dimensional array detectors in the fluid, and acquiring a plurality of images of the further subsets of particles as they flow past the further two-dimensional array detectors in the fluid.

In another general aspect, the invention features a particle characterization instrument that includes a first two dimensional detector, a second two-dimensional detector, channel walls mounted to the first and second two-dimensional detectors for defining a first channel to hold a fluid containing a sample in contact with the first two-dimensional detector and defining a second channel to hold the fluid containing a sample in contact with the second two-dimensional detector, wherein the first channel and the second channel are hydraulically connected and have a different cross-section, a driver to move the fluid through the channels, and an imaging illumination source positioned to illuminate particles in the fluid while it is in contact with the two-dimensional detector. In preferred embodiments the channel walls can define serial channels.

In a further general aspect, the invention features a particle characterization instrument that includes means for causing a first subset of the suspended particles to flow past a first two-dimensional array detector, means for illuminating the first subset of suspended particles as they flow past the first two-dimensional array detector in the fluid, means for acquiring a plurality of images of the first subset of particles as they flow past the first two-dimensional array detector in the fluid, means for causing a second subset of the suspended particles to flow past a second two-dimensional array detector, means for illuminating the second subset of suspended particles as they flow past the second two-dimensional array detector in the fluid, and means for acquiring a plurality of images of the second subset of particles as they flow past the second two-dimensional array detector in the fluid.

Systems according to the invention can help to characterize a variety of different particulate materials in industrial settings, such as in the manufacture of pharmaceuticals. This can help to provide ongoing quality control and quality assurance in the manufacture of such materials.

In a further general aspect the invention features a heterogeneous fluid sample characterization method, the method comprising:

inserting a probe into a first of a plurality of heterogeneous fluid samples;

drawing at least a first portion of the first sample into the probe and past a two-dimensional array detector;

illuminating the first portion of the first sample as it is drawn past the two-dimensional array detector;

acquiring at least a first image of the first portion of the first sample as it is drawn past the two-dimensional array detector;

inserting the probe into a second of the plurality of heterogeneous samples;

drawing at least a first portion of the second sample into the probe and past a two-dimensional array detector;

illuminating the first portion of the second sample as it is drawn past the two-dimensional array detector in the fluid; and acquiring at least a first image of the first portion of the second sample as it is drawn past the two-dimensional array detector in the fluid.

The method may include the step of suspending solid particles or mixing a plurality of fluids in the plurality of fluid samples to thereby introduce heterogeneity in those samples.

The method may include a further step of drawing one or more portions of the samples to mix the samples.

The step of drawing one or more portions of the samples to mix the samples may be carried out after the steps of acquiring. The method may further include further steps of acquiring images after the further step of drawing, the further step of drawing being performed with a higher flow rate than the steps of drawing.

The method may further include the step of discarding the first portion of the first sample after the step of acquiring a first image of the first sample and before the step of drawing a first portion of the second sample. The method may include washing the probe after discarding the first portion of the first sample and before drawing a first portion of the second sample.

The method may further include steps of automatically positioning the probe relative to the first and second samples. The steps of automatically positioning may be performed by an x-y stage or by an x-y-z stage.

The step of illuminating may include a step of strobing a source (e.g. a light source) for a plurality of short acquisition periods and acquiring the images during the plurality of short acquisition periods. The acquisition periods may for example be less than one second, and are preferably less than one tenth of a second.

The method may include the step of displaying the acquired images of the particles in a sorted thumbnail view.

The steps of suspending, causing, acquiring, and applying may be carried out as part of a molecular microbiological method, performed for a biological sample, pharmaceutical sample, industrial sample or as part of a manufacturing process quality control evaluation.

The steps of suspending, causing, acquiring, and applying may be applied to evaluate a dispersion step.

The step of applying a particle characterization function may apply a contaminant detection function or a counterfeit detection function.

The step of causing the suspended particles to flow past a two-dimensional array detector may cause the suspended particles to flow along a single flow path having a profile that includes a detector flow region and a pair of bypass channels, or to flow along a path with substantially no zero-flow regions. The suspended particles may be caused to flow at a flow rate of at least one liter per minute or at a flow rate of less than about two milliliters per minute.

The method may include the step of applying a statistical function to image data from the two-dimensional array detector to gage heterogeneity. The statistical function may involve calculating a measure of entropy in the plurality of acquired images. The measure of entropy may be calculated from a sum of probabilities of pixel values or differences between adjacent pixel values in each acquired image being a given value.

The fluid may be a liquid, and may contain solid particles or agglomerates suspended in a liquid, or alternatively droplets of a first liquid dispersed in a second liquid, the first and second liquids being immiscible.

In a further general aspect the invention features a heterogeneous fluid sample characterization method, comprising:

illuminating the heterogeneous fluid sample;

causing the heterogeneous fluid sample to flow past a two-dimensional array detector;

acquiring at least one image of the illuminated heterogeneous fluid sample; and extracting a summarizing metric from the images.

The step of extracting a summarizing metric may include extracting information about particle size or flow or extracting a dispersion metric from the images. The summarizing metric may include information about particle numbers or particle density. The step of extracting a dispersion metric from the images may apply an entropy function to the images.

The method may include the step of dispersing the heterogeneous fluid sample. The step of dispersing may for example involve mixing the heterogeneous, fluid sample or sonicating particles in the heterogeneous fluid sample, i.e. applying ultrasound energy to the fluid sample.

The step of acquiring an image may take place in a flow from an in-line particle disperser, and the method may further include the step of returning the particles to the in-line particle disperser after the step of acquiring. The method may include the step of reporting the detection of a predetermined state of the dispersion metric. The method may include the step of reporting the detection of a stabilization of the dispersion metric. The method may include adjusting a process that is applied to the fluid based on the dispersion metric in real time. The method may include the step of performing a second measurement on the heterogeneous fluid sample. The second measurement may be a laser diffraction measurement. The dispersion metric may be used to trigger the second measurement in real time. The dispersion metric may be used to validate the second measurement. The method may include the step of reporting the detection of a predetermined state of the dispersion metric.

The method may include the step of reporting the detection of a stabilization or detection of a rate of change of the dispersion metric. The method may include adjusting a process that is applied to the fluid based on the dispersion metric in real time. The method may include the step of performing a second measurement on the heterogeneous fluid sample. The second measurement may be a laser diffraction measurement. The dispersion metric may be used to trigger the second measurement in real time. The dispersion metric may be used to validate the second measurement. The step of extracting a dispersion metric from the images may apply an entropy function to the images.

DETAILED DESCRIPTION OF THE INVENTION

Figure 1:
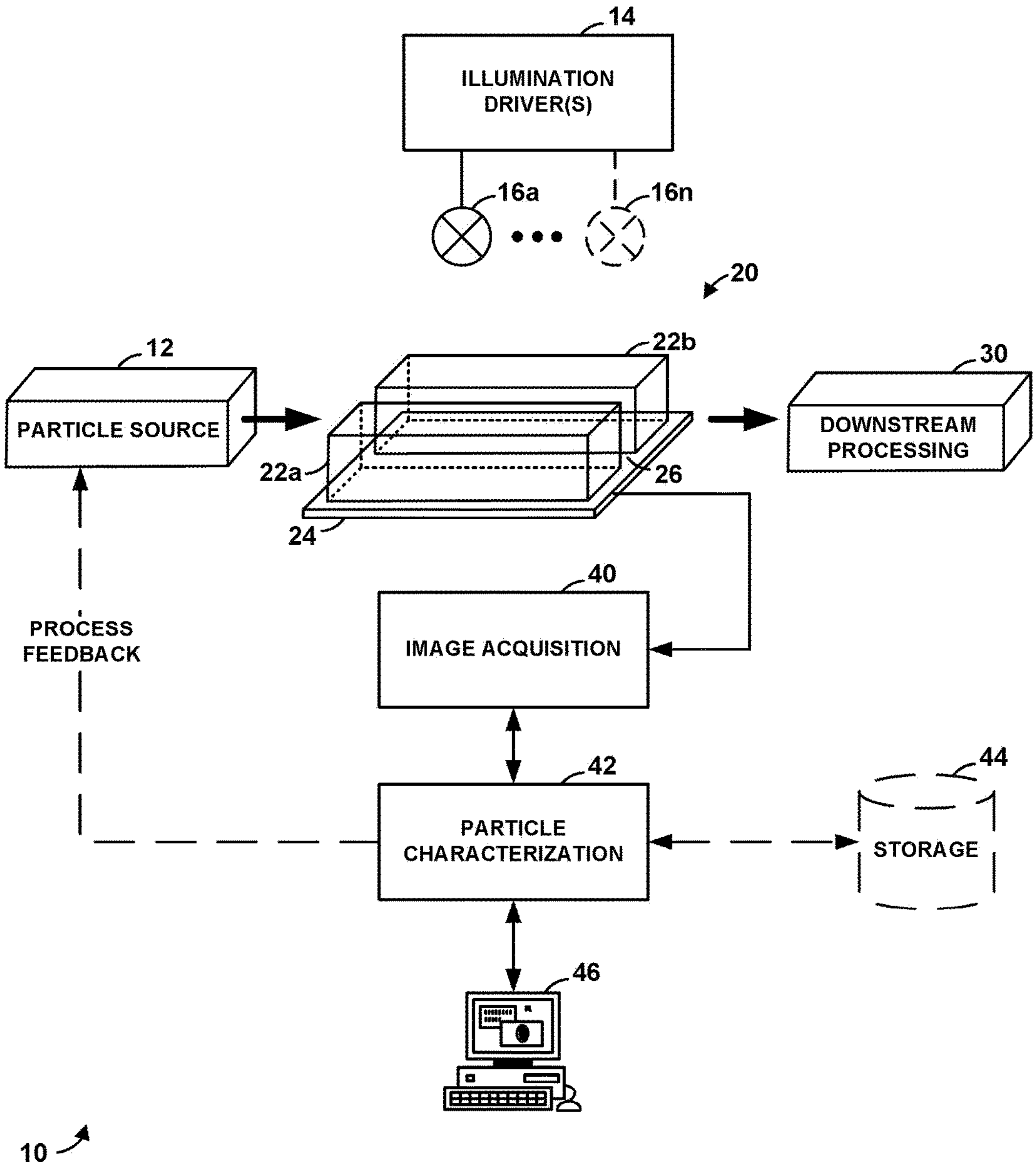
FIG. 1 is a block diagram of a particle characterization system according to the invention.

Referring to FIG. 1, a particle characterization system 10 according to the invention characterizes particles from a particle source 12, such as an industrial process. The process can perform a number of different types of operations on the particles, such as creating them, modifying them, and/or mixing the particles. In one example, the process is a dispersive process that disperses the active and inactive ingredients of a pharmaceutical agent.

The system 10 also includes one or more illumination drivers 14 that drive one or more illumination sources 16*a* . . . 16*n*. These sources can be of a variety of different types and can exhibit a variety of different spectral characteristics. Some examples include visible wavelength illumination sources, narrowband coherent fluorescence excitation sources, or even simple ambient light sources. In a preferred embodiment, the illumination driver 14 includes strobing circuitry that allows short illumination pulses to be produced.

The particle source 12 provides particles that are suspended in a liquid that is passed through a microfluidic detection cell 20. The cell 20 includes a hydraulic channel 26 that passes above or alongside a two-dimensional array detector 24, such as a CCD or CMOS array detector. This cell 20 can be fabricated using a variety of different techniques, such as by machining a metal block or molding a plastic part to define a channel between a pair of walls 22*a*, 22*b* above the detector 24. The suspended particles can be conveyed through the microfluidic system in a variety of known ways, such as by pumping, gravity, or by capillary action.

Figure 2A:
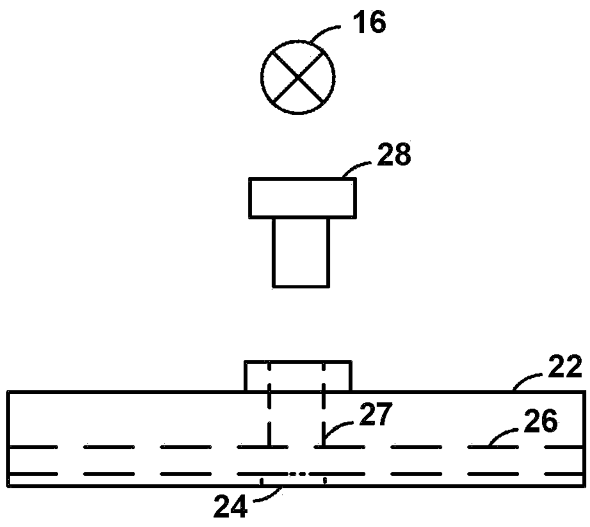
FIG. 2A is a diagrammatic side-view sketch of a microfluidic cell block for use with the particle characterization system of FIG. 1.
Figure 2B:
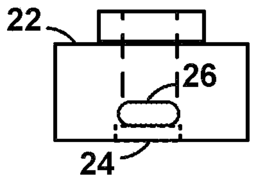
FIG. 2B is a diagrammatic end-view sketch of the microfluidic cell block of FIG. 2A.
Figure 2C:
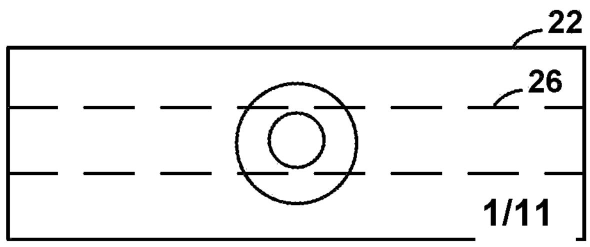
FIG. 2C is a diagrammatic top-view sketch of the microfluidic cell block of FIG. 2A.

Referring to FIG. 2, in one embodiment a cell channel block 22 can be machined in an aluminum block with a rectangular channel 26, with rounded corners, passing through its length just above its bottom. A recess in the bottom of the block holds a two-dimensional detector 24 below a window shaft 27. A window bolt 28 can then be slid into the window shaft 27 such that the bolt 28 protrudes into the channel 26 and thereby narrows it at a portion of the block 22. The window bolt 28 has a transparent bottom through which light from a source 16 can shine into the narrow portion of the channel. In one embodiment, the height of the window bolt is adjustable.

Figure 3:
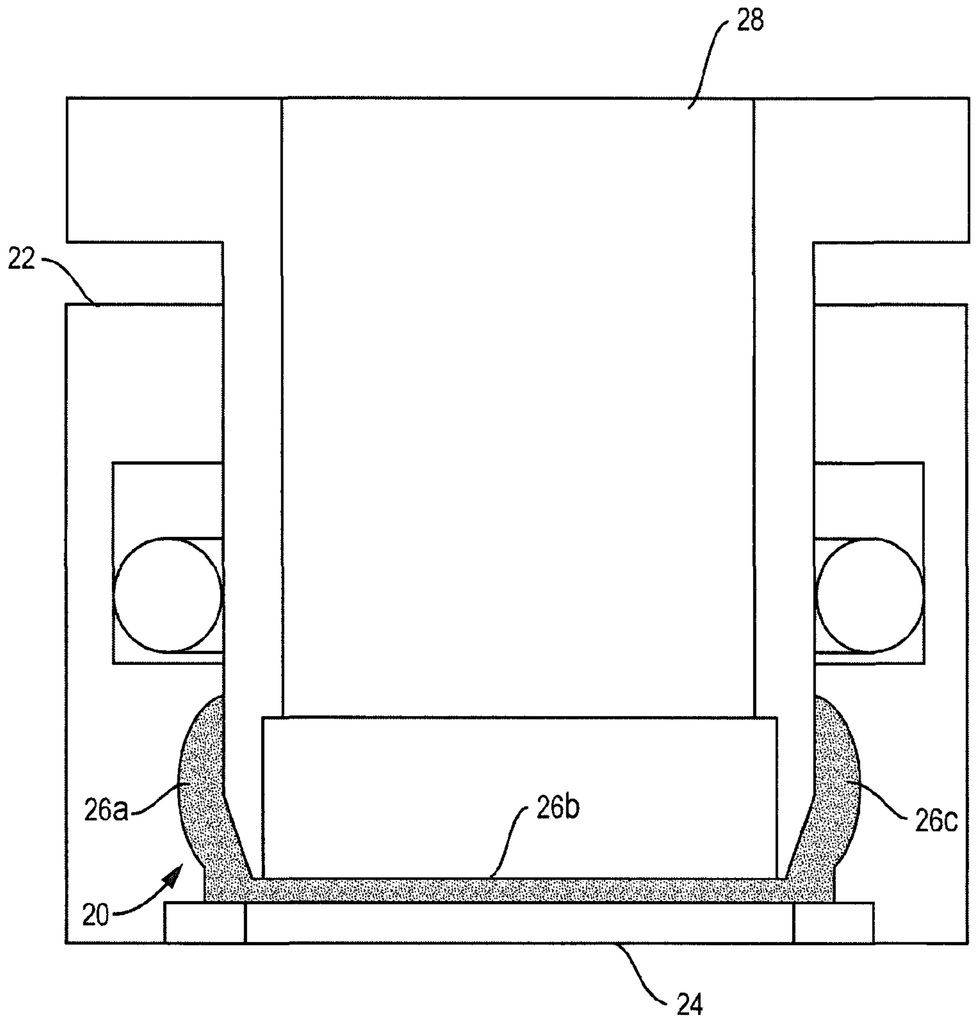
FIG. 3 is an enlarged, partial cross-section of the microfluidic cell block of FIG. 2 that cuts through its window bolt perpendicularly to the direction of flow.

Referring to FIG. 3, the bolt creates an "eared" channel 26 that includes a first ear 26*a* on one side of the window bolt 28 and a second ear 26*c* on the other side of the bolt 28. Between the two ears and below the bolt 28 is an imaging region 26*b*. This region is between the lower transparent surface of the window bolt 28 and the upper surface of the detector array 24. In a general aspect therefore, the channel 26 has a profile that includes a detector flow region 26*b* and a pair of bypass channels 26*a*, 26*c* on either side of the detector flow region 26*b*, the detector flow region being optionally defined by a space between the two-dimensional array detector 24 and an end surface of an adjustable bolt 28 extending into a microfluidic detection cell 20 of the particle characterization instrument. The adjustable bolt 28 is preferably configured to allow illumination of the detector flow region 26*b* by an illumination source (see FIG. 1) through an end surface of the bolt 28.

This channel shape has been found to work well in the relatively high pressures that are found in some industrial processes, because it does not appear to cause aggregation or segregation, which can plague other geometries. This is believed to be at least in part because this channel shape does not appear to exhibit any zero-flow regions. The ears or bypass channels 26*a*, 26*c* also provide an escape area for occasional large contaminant particles that might otherwise block the channel, which is required to be narrow in order to ensure a clear image of the particles in suspension. Simulations have confirmed that, unlike with other geometries, different sizes of particles in a mixture will tend to flow evenly into the imaging area instead of becoming segregated, and that larger contaminant particles will generally make their way into the ears instead of building up in front of the window bolt.

The cell channel block 22 may be glued to the array detector 24 with an epoxy cement, although other methods of attachment are of course possible. It is contemplated that a larger channel block could be glued to more than one detector to allow for a larger single detection area or more than one detection area. These sets of detectors can help a system to acquire more data per unit time because large array detectors tend to take a long time to read. These sets of detectors can also provide apparent flow rates, which can be correlated with full flow rates. Detectors can be oriented at 90 degrees, as well, so as to provide different views of a same field of particles.

Referring again to FIG. 1, after passing through the microfluidic detection cell 20, the suspended particles move on to downstream processing 30, which can include further operations on the particles, further characterization of the particles, or both. In one embodiment, the suspended particles are provided to an off-the-shelf laser diffraction system for to further characterize them after the microfluidic detection. But the microfluidic detection can also take place after one or more other types of detection, or even in parallel with them. Detection systems that can provide information that is complementary to the microfluidic cell include any type of optical detection system that can operate on suspended particles, such as laser diffraction, Dynamic Light Scattering (DLS), or Static Light Scattering (SLS).

Laser diffraction is a well known technique for determining particle sizes. In this technique, light from a laser is shone into a suspension of particles. The particles scatter the light, with smaller particles scattering the light at larger angles than bigger particles. The scattered light can be measured by a series of photodetectors placed at different angles. This is known as the diffraction pattern for the sample. The diffraction pattern can be used to measure the size of the particles using light scattering theory that was developed in the early 20th century by Mie. As the instrument measures "clouds" of particles rather than individual ones, it is known as an "ensemble" technique.

DLS is also a well-known ensemble technique in which suspended particles scatter laser illumination. In this kind of technique, however, the time dependent fluctuation of the scattering is measured to understand Brownian motion in the sample. This provides information about the dynamic properties of particle systems, such as the hydrodynamic radius of the particles.

SLS statically measures scattered light intensity of light at different angles to obtain the molecular weight of suspended particles. Some instruments, such as the Zetasizer Nano, available from Malvern, Inc. of Malvern, UK, can perform both DLS and SLS measurements.

The combined approaches presented above can provide a level of insight into a particulate system that two separate measurements could not provide. Combining microfluidic detection with laser diffraction, for example, can allow a user to see images of particles before or after they pass through the laser diffraction system. While the laser diffraction system alone can provide precise size values, it is an ensemble technique that tends to favor high mass particles over smaller ones. With images coupled to these measurements, however, one can understand better what the laser diffraction measurement means.

In one embodiment, particles or groups of particles meeting one or more predetermined criteria can first be marked as preapproved using one upstream technique. Data from the application of one or more downstream techniques then need only be retained for particles that are preapproved. The preapproval can even gate the downstream technique so as to prevent any downstream acquisitions from taking place for non-preapproved particles.

An image acquisition subsystem acquires images from the two-dimensional array detector 24. This subsystem can be synchronized with the source in the case of strobed illumination, allowing for high-speed acquisition of particle images. With a suitable strobe sequence, the system can even acquire more than one image as it passes through the channel.

A particle characterization subsystem 42 can apply one of a number of different particle characterization functions to the particles, such as by categorizing them into defined morphological and/or color categories. Particles can also be counted and their occurrences can be statistically analyzed. The table below lists various illustrative ways in which particles can be characterized.

| Parameter | Example value | Definition |
|---|---|---|
| ID | 516 | Unique ID of the particle - allocated in the order that the particles are detected |
| Magnification | 2.50 | Magnification used to make the measurement |
| CE diameter (μm) | 904.14 | The diameter of a circle with the same area as the particle |
| Length (μm) | 1306.35 | All possible lines from one point of the perimeter to another point on the perimeter are projected on the major axis (axis of minimum rotational energy). The maximum length of these projections is the length of the object. |
| Width (μm) | 678.54 | All possible lines from one point of the perimeter to another point on the perimeter are projected on the minor axis. The maximum length of these projections is the width of the object. |
| Max. Distance (μm) | 1318.07 | Largest distance between any two pixels in particle |
| Perimeter (μm) | 3619.42 | Actual perimeter of particle |
| Major axis ° | 105.52 | Axis of minimum rotational energy |
| Area ($\mu m^2$) | 371550.78 | Actual area of particle in sq. microns |
| Area (pixels) | 215018 | Number of pixels in particle |
| Circularity | 0.785 | Circumference of equivalent area circle divided by the actual perimeter of the particle = $2\sqrt{(\pi\ \text{Area})}$/Perimeter |
| HS Circularity | 0.616 | High sensitivity circularity (circularity squared) = 4 $\pi$Area/perimeter$^2$ |
| Convexity | 0.919 | Convex hull perimeter divided by actual particle perimeter |
| Solidity | 0.905 | Actual particle area divided by convex hull area |
| Aspect ratio | 0.519 | Width divided by length |
| Elongation | 0.461 | 1 − aspect ratio |
| Intensity mean | 61.310 | Average of all the greyscale values of every pixel in the particle |
| Intensity standard deviation | 29.841 | Standard deviation of all the greyscale values of every pixel in the particle |
| Center x position (μm) | 271.5 | x co-ordinate of center of mass of particle |
| Center y position (μm) | 186.3 | y coordinate of center of mass of particle |

Other characteristics can also be measured, and any of the measured characteristics and associated counts and/or statistical information can then be used in a variety of ways to evaluate the particles. For example, they can be compared with stored known-good criteria to evaluate whether the process is operating within a predetermined specification, they can be shown to the user on a workstation as images or in sortable thumbnail views, or they can be used to adjust the process.

The system can also calculate average grey scale values for the full field (average pixel brightness and pixel standard deviation) in order to provide a measure of homogeneity. A relatively steady average brightness and standard deviation suggests a relatively steady flow of particles. A change in brightness (or standard deviation) implies a change in particle flow. A few large particles in an otherwise steady flow of small particles, for example, should cause a lower average brightness (and average brightness & standard deviation is easy to plot). This simple calculation won't provide as much information as size/morphology calculations provide, but the calculation can be done without requiring any additional hardware. One type of simple calculation that can be performed is to calculate a dispersion metric, as described below in connection with FIGS. 11-14.

Through the use of more than one source, the system can acquire different types of information about the suspended sample particles. For example, a first strobed acquisition can acquire successive visible-wavelength images of a particle in the channel. A second narrow-band source can then be turned on to detect any particles that fluoresce or to detect scattering patterns.

Figure 6:
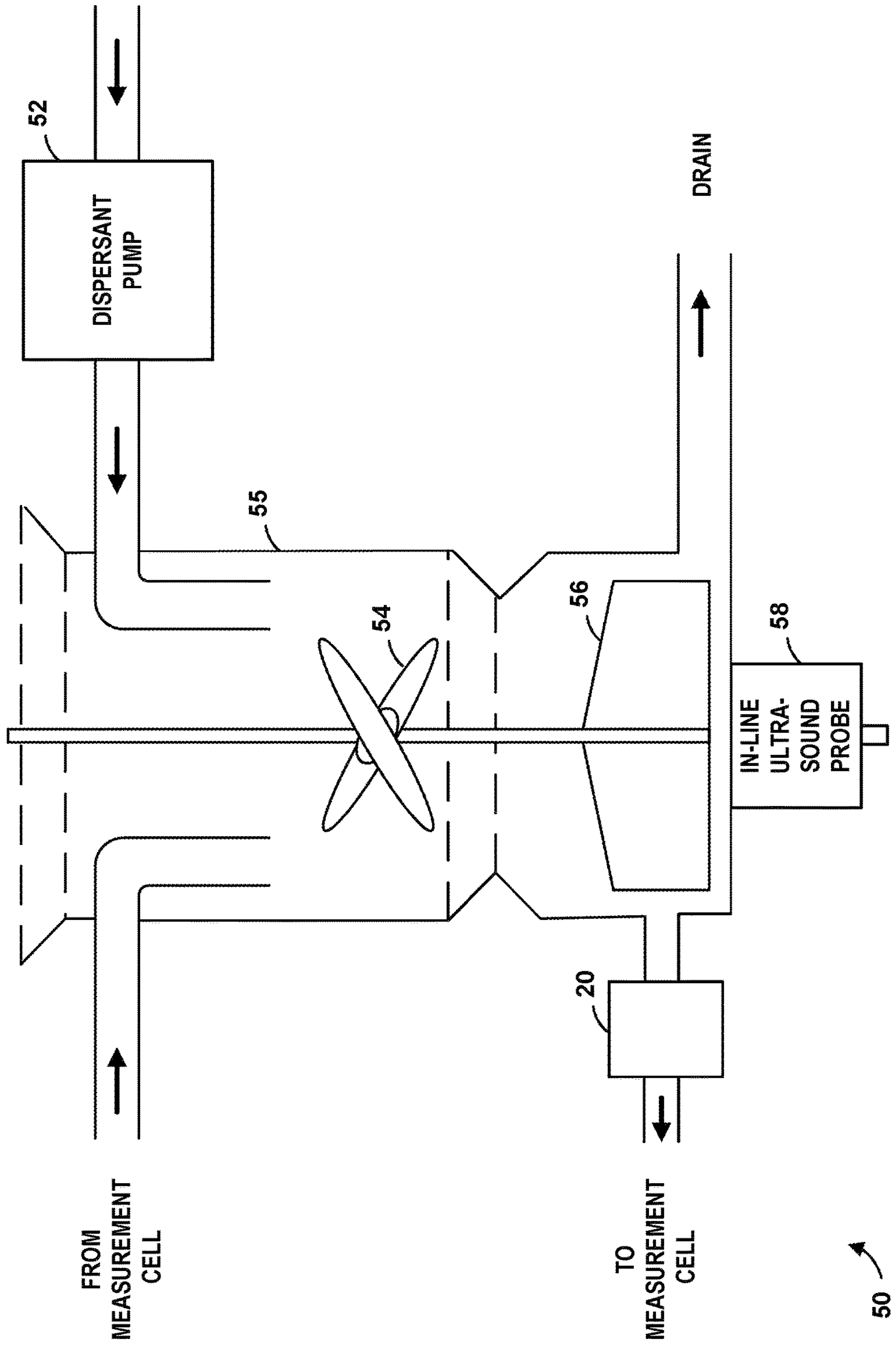
FIG. 6 is an illustrative wet dispersion unit schematic for use with the particle characterization system of FIG. 1.

Systems according to the invention can be applied to a number of different types of processes, such as Metals, Mining, and Minerals (MMM) applications or the manufacture of pharmaceuticals, personal care products, foodstuffs, pigments, and biomaterials. An example of an application to a wet dispersion process is shown in FIG. 6. More specifically, a wet dispersion unit 50 includes an optional dispersant pump 52 that feeds a top end of a sample tank 55 that is equipped with a central stirrer 54, and a centrifugal pump 56 and an in-line ultrasound probe (or "sonication system") 58 at the bottom end of the tank. The tank also includes a measurement branch line that begins at the bottom of the tank and returns back to the top of the tank as well a as a drain line at the bottom of the tank. The measurement loop includes a microfluidic detection cell 20 and another measurement cell, such as one for an off-the-shelf laser diffraction system.

In operation, the dispersant pump 52 feeds dispersant into the sample chamber 55, the stirrer 54 mixes particles into the dispersant, and the in-line ultrasound probe 58 breaks up the particles. The centrifugal pump 56 circulates the fluid so that it can be repeatedly stirred and sonicated. The microfluidic detection cell 20 and the other cell can monitor the dispersed particles as they are recirculated.

Although this figure shows the detection cell at the intake of a complementary detection system, the detection cell can also be positioned in a return conduit from the complementary detection system. In some embodiments, the two complementary detection processes can even take place in parallel or on separate branch lines from the process conduit.

A channel block as shown in connection with FIGS. 2-3 was glued to a 5-megapixel iPhone® camera chip with an epoxy cement. A suspension was made up of a mixture of 80 micron and 20 polystyrene microspheres with the four times as many of the smaller microspheres than the larger ones suspended in water. This suspension was pumped through the channel at a 2-liter-per-minute flow rate.

Figure 4:
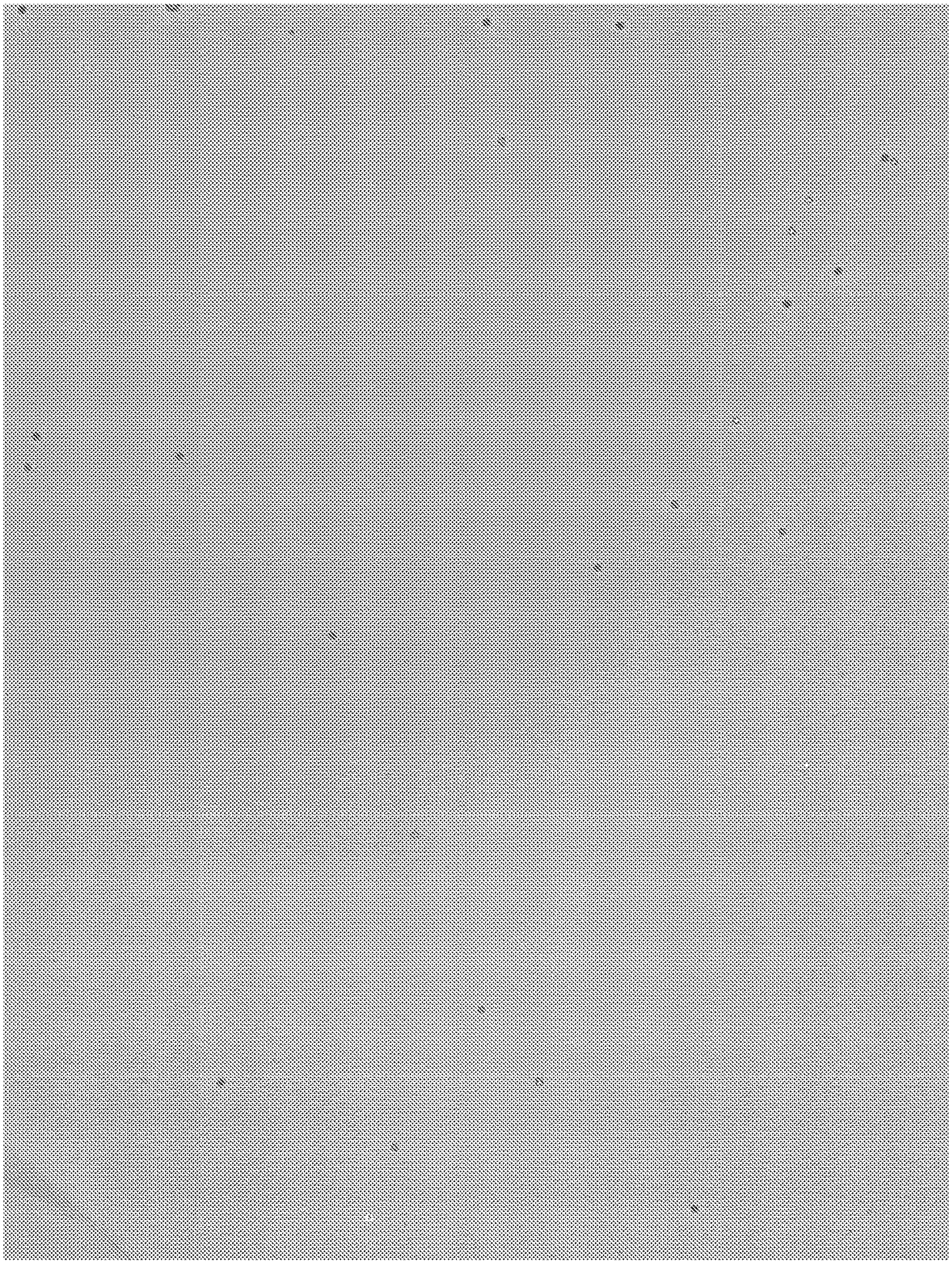
FIG. 4 is an image acquired using the microfluidic cell block of FIG. 2 in the particle characterization system of FIG. 1.
Figure 5:
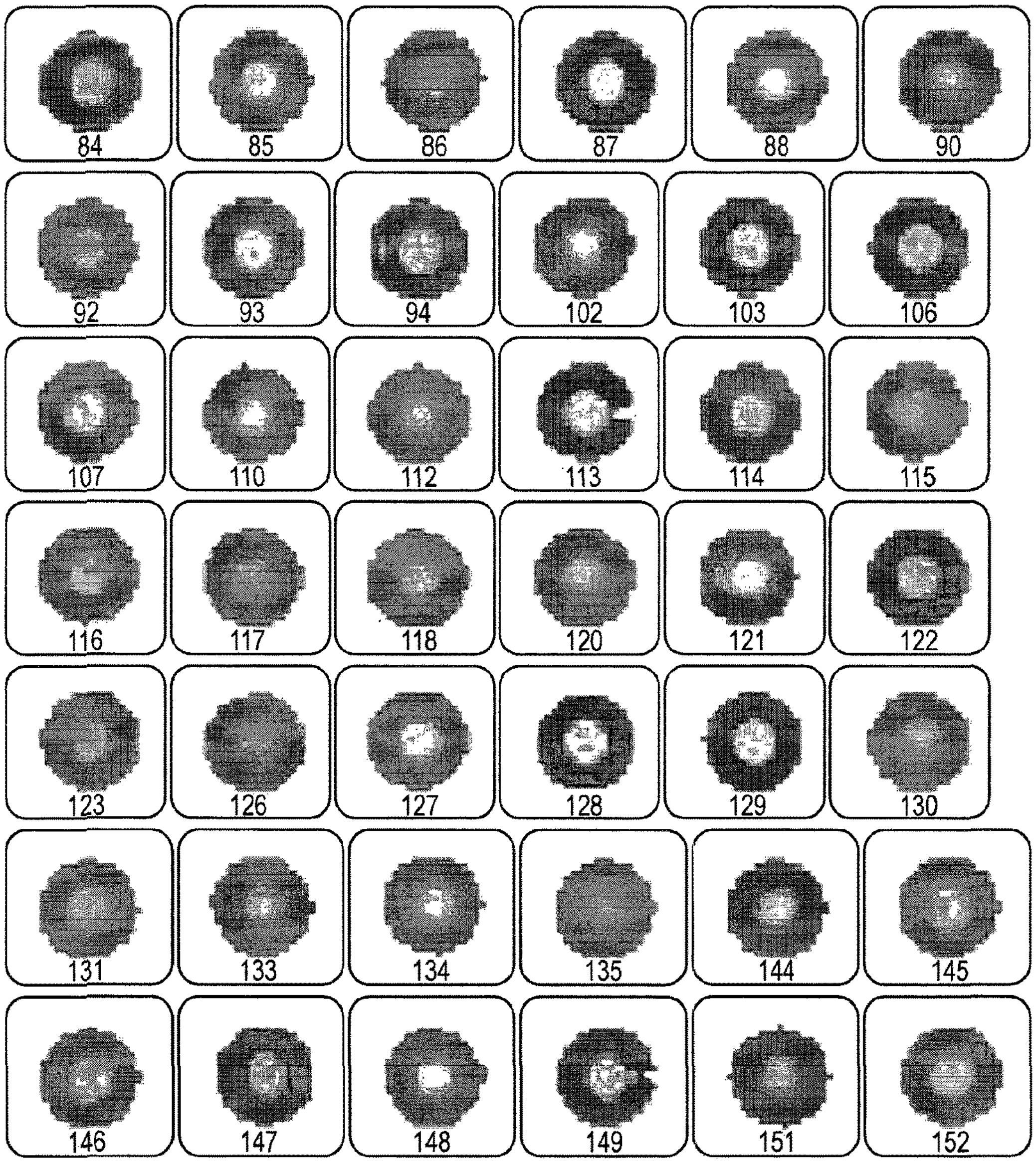
FIG. 5 is a sorted thumbnail view of particles in an image such as the one shown in FIG. 4.

The suspension was illuminated with a strobed, white-light LED. Instead of using the chip's built-in shuttering capabilities, its sensor was left in acquisition mode and strobe pulses were used to define the acquisition period. The image shown in FIG. 4 was acquired, and the thumbnail set shown in FIG. 5 was assembled.

The suspension was also passed through a Mastersizer® laser diffraction system, available from Malvern Instruments Limited of Malvern, UK. As predicted, the measurement from this system tended to favor the larger particles. But with the images from the microfluidic cell, this measurement can be corrected or put in the proper context.

The particle images can also be sorted according to their morphological characteristics as discussed in more detail in U.S. Pat. No. 8,111,395, which is herein incorporated by reference. Because the detector is capable of acquiring a huge amount of data, a local processor coupled to the detector can extract images of the particles themselves and only transfer these to a user computer for characterization. This can substantially reduce the amount of data transferred by eliminating transfers of white space.

Operations on the images as well as control operations, including control of the drivers, can be performed in connection with special-purpose software programs running on general-purpose computer platforms in which stored program instructions are executed on a processor, but they could also be implemented in whole or in part using special-purpose hardware. And while the system can be broken into the series of modules and steps shown for illustration purposes, one of ordinary skill in the art would recognize that it is also possible to combine them and/or split them differently to achieve a different breakdown.

The particle characterization system 10 can provide a software control that allows it to perform a flat-field correction in the presence of sample particles without purging or flushing. This flat field correction adjusts for imaging error sources, such as uneven illumination, surface reflections, defects (e.g., surface scratches), and non-uniform pixel response of the detector. Performing this type of correction on the fly without purging the instrument can significantly speed up operation and can simplify hookups by eliminating the need for a dedicated purge or flush path.

The on-the-fly flat-field correction can be performed in either of two ways. In the first approach, the system acquires a large number of frames and averages corresponding pixels in those frames. Since particles in each image are reasonably sparse, and will appear at random positions during each frame, the averaging will reduce the impact of any particles. In a general aspect therefore, performing the flat-field correction may involve deriving an average image from a plurality of calibration images and correcting sample images of the particles using the derived average image.

More specifically, the intensity of particle imprint is generally reduced to about 1/N, where N is the number of frames, so a higher number of frames improves the result. This approach has been tested for 2% obscuration with different numbers of frames from 10 to over 100 frames. Good results appear to require at least 50 frames, and particle contribution is very difficult to see in the 100-frame average. With a system that can acquire 7.5 frames per second, reasonable results could therefore be achieved in 15-30 seconds. In a general aspect therefore, the number of calibration images used in deriving the average image is preferably 50 or more, and may optionally be up to 100 images.

In the second approach, a smaller number of frames are averaged without including those parts of the image where particles are present. In this approach a threshold level is set that indicates the presence of a particle. By simply eliminating regions of a frame that are outside of that threshold on a per-frame basis, a small number of frames can be averaged to get a good background estimate. One simple way of doing this is to look at frame-to-frame differences—the presence of a particle in any causes a large difference (in the region obscured by the particle) from the prior frame. This approach would likely benefit from the inclusion of a measurement under known conditions (e.g., factory conditions). This method is outlined below:

Step 1: collect N consecutive frames

Step 2: for each pixel, calculate the mean and standard deviation σ across all N frames Step 3: for each pixel, iterate through its values and reject values that differ from the mean by more than $q*\sigma$, where q is determined experimentally (typically, q=1)

Step 4: for each pixel, average the values remaining after outlier rejection.

The "frame" composed of averages represents the reconstructed background.

In a general aspect therefore, the flat-field correction may be performed by acquiring a plurality of calibration images and deriving an average of the plurality of calibration images after removing portions of each of the calibration images having pixels that differ in value from a mean value by more than a predetermined factor. The predetermined factor may for example be a multiple of a standard deviation of each calibration image. The multiple may be one. The value of the pixels may for example be a brightness value.

The outlier removal method can be performed on fewer frames (e.g., 10-20 frames), and the resulting background image is free from "traces" of particles that are visible in the averaging method. Part of the computation can be performed while acquiring data (summing pixel values and squared pixel values for the standard deviation). The process can also be made to be massively parallel, and thus lend itself to General-Purpose Computing On Graphics Processing Units (GPGPU) acceleration. The outlier removal method has the disadvantage of higher memory usage, because all collected frames remain in memory for the entire process, and it is computationally more expensive than the averaging method. In a general aspect therefore, the number of calibration images acquired for this flat-field correction method may be fewer than 50, and may be between 10 and 20.

Figure 7:
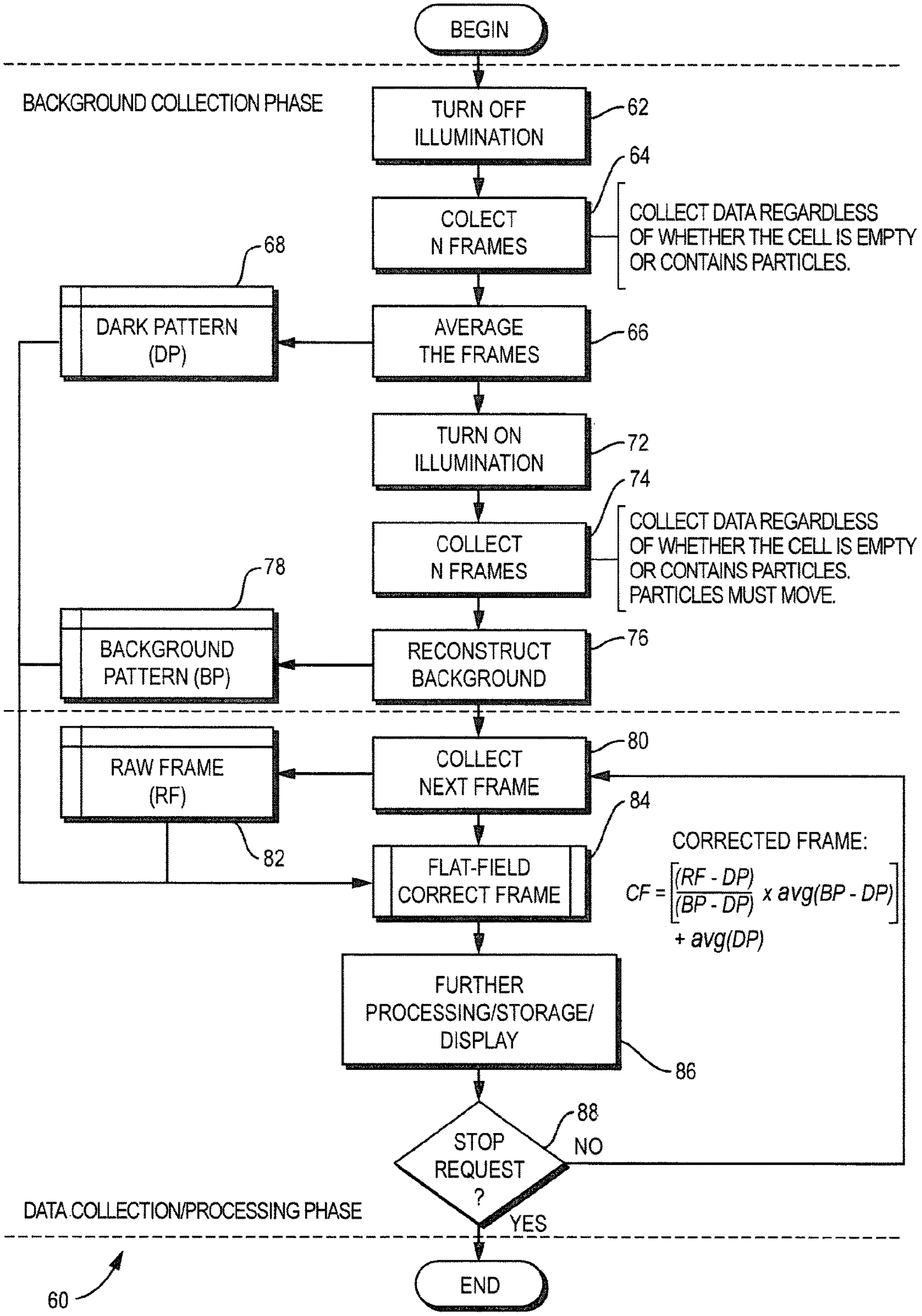
FIG. 7 is a flowchart illustrating the acquisition and processing of flat-field corrected frames for the particle characterization system of FIG. 1.

Referring to FIG. 7, the particle characterization system 10 begins a set of flat-field corrected acquisition operations 60 by turning off the illumination (step 62). It then acquires a number of frames, such as 100 frames (step 64), and averages them using one of the averaging approaches described above (step 66). The result is stored as a dark pattern data set (step 68).

The particle characterization system 10 then turns on the illumination (step 72). It then acquires a number of frames, such as 100 frames (step 74), and averages them using one of the averaging approaches described above (step 76). The result is stored as a background pattern data set (step 78).

The particle characterization system 10 can then acquire a sample image frame (step 80) and store it as raw frame data set (step 82). This raw frame data set (RF) is then corrected using the dark pattern data set (DP) and background pattern data set (BP). The correction can be calculated using the following formula:

$$CF = \left[\frac{(RF - DP)}{(BP - DP)} * avg(BP - DP)\right] + avg(DP)$$

The corrected frame (CF) can then be stored, displayed, or otherwise processed (step 86). If further sample image frames are needed the process of acquisition and correction can be repeated (see step 88). It is possible to derive simpler flat-field correction solutions that may be more computationally efficient, although they may not behave as well as the exact solution above, particularly for non-uniform illumination.

Figure 8:
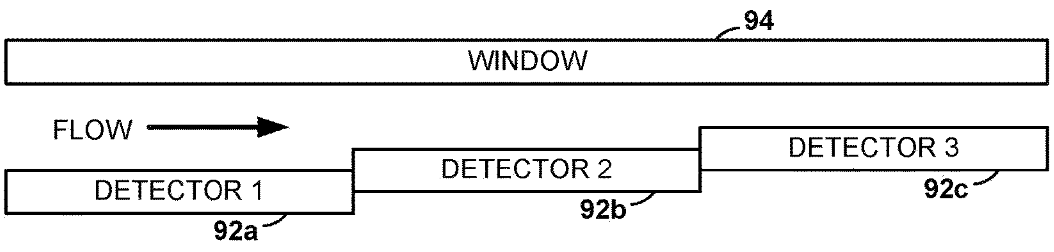
FIG. 8 is a side-view block diagram of a three-channel serial multichannel particle characterization system according to the invention.
Figure 9:
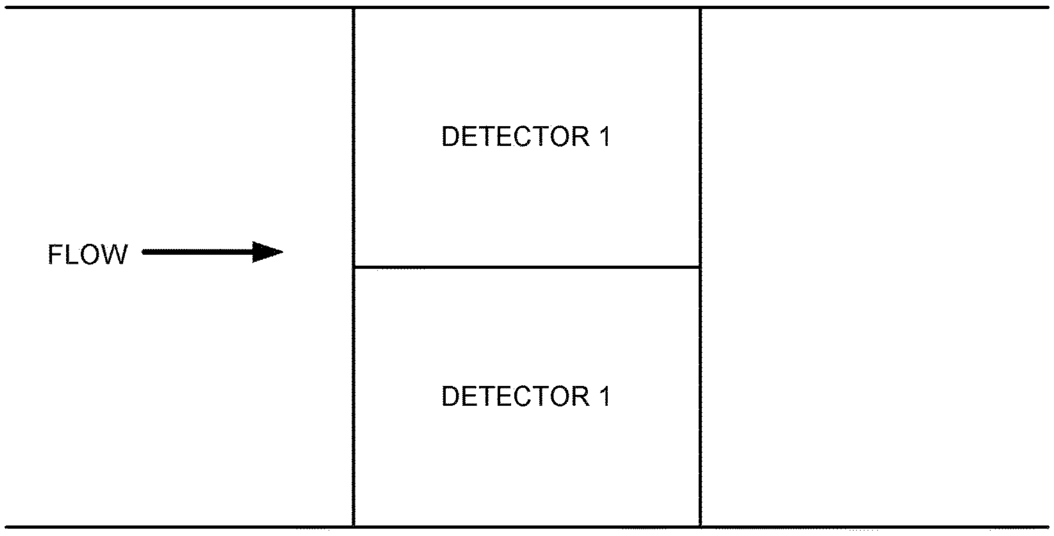
FIG. 9 is a top-view block diagram of a two-channel parallel multichannel particle characterization system according to the invention.

Referring to FIG. 8, particle characterization systems according to the invention can perform more than one type of measurement in a serial or parallel fashion. For example, a three-channel serial multichannel particle characterization system 90 includes three back-to-back detectors 92*a* . . . 92*c* positioned under a single illumination window 94 (although multiple illumination windows and/or multiple illumination sources may also be used). In operation, this system allows the first detector 92*a* to sample larger particles and subsequent detectors to sample smaller and smaller ones, with larger ones passing through the bypass channels. The results can be used separately or combined. As shown in FIG. 9, although serial configurations are presently contemplated as preferable, a parallel multichannel particle characterization system 96, in which the flow is divided across different side-by-side channels, can also be built.

Multichannel particle characterization systems can be built with any suitable number of detectors and it may also be possible to vary channel dimensions over the length of a single detector. These types of systems can also be built in a variety of ways. They can be built as a compound structure as illustrated in FIG. 8, for example, or they could be built with a series of microfluidic detection cells 20 (see FIGS. 1 and 2) connected in series with tubing. The systems can include one or more eared bypass channels for some or all of the detectors, depending on system requirements. Smaller-sample systems will tend to have lower bypass flows or even no bypass flow, for example, and larger re-circulating systems will have larger bypass flows.

Figure 10:
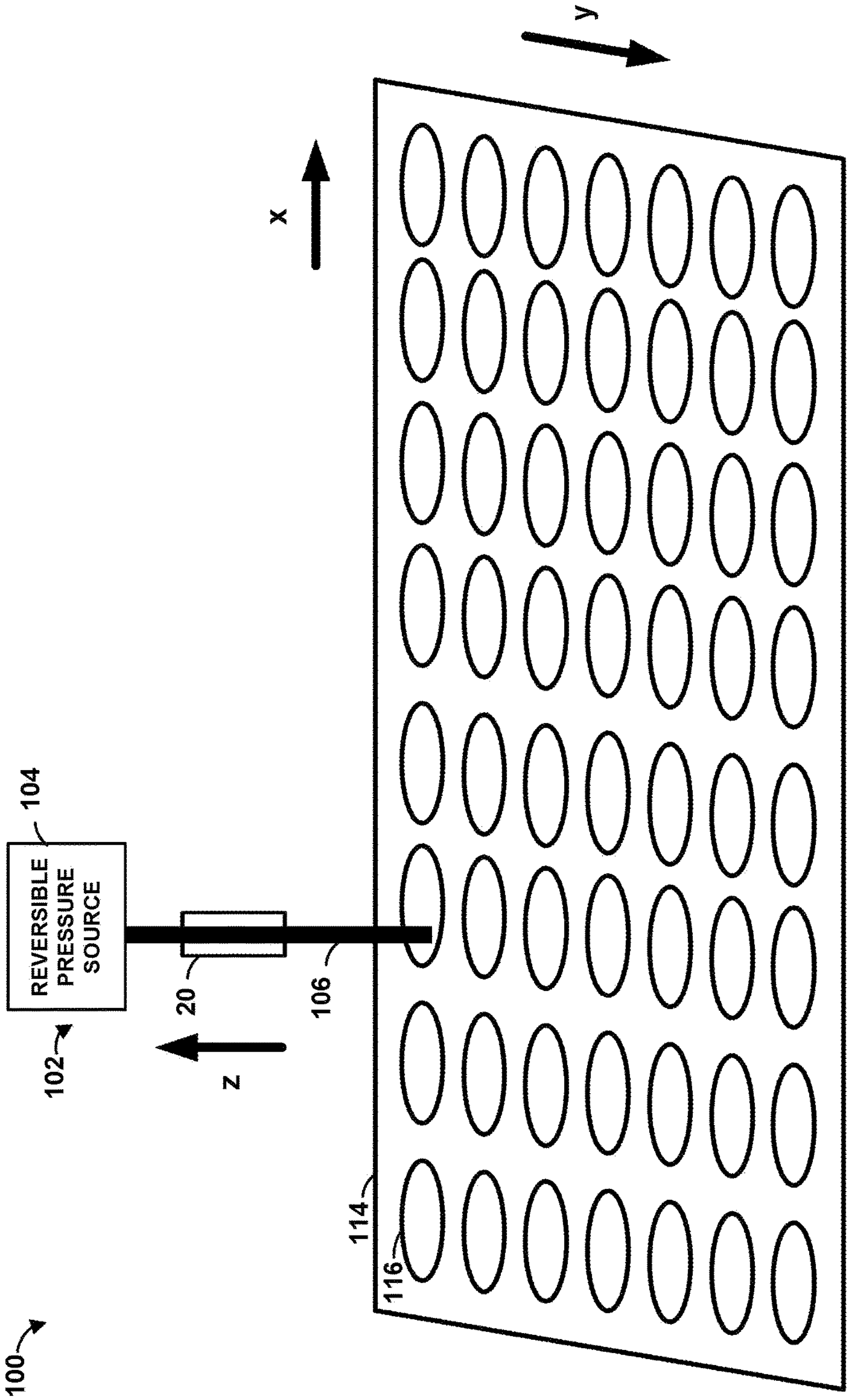
FIG. 10 is a block diagram of an embodiment of a high-throughput particle characterization system according to the invention.

Referring to FIG. 10, a high-throughput version of the particle characterization system can also be built using one or more microfluidic detection cells. For example, a single-channel system 100 according to the invention uses a sampling probe 102 to perform successive measurements on a number of liquid samples held in different vessels, such as wells 116 of a multi-well plate 114 or carousel. The system 100 uses a reversible pressure source 104 that is hydraulically connected to a sipper tube 106 via an in-line microfluidic detection cell 20. While a single-channel system is shown here, different kinds of multichannel high-throughput systems can also be designed.

In this embodiment, an off-the-shelf x-y-z stage is provided to successively position the samples under the probe, although other types of mechanisms can be used to position the vessels and probe relative to each other. Wash and waste vessels can also be provided, either in the plate, or separately.

In an illustrative operation sequence, the x-y-z stage begins by positioning a first of the wells below the probe 102 to select a first sample and the pressure source 104 draws the sample into the sipper tube 106 and through the detector 20. The image acquisition module then acquires an image of the first sample from each of the microfluidic detection cells. The first sample can then be returned to the first well or it can be discarded into a waste well, and the probe can be washed in a wash well. If there are more samples to process, the x-y-z stage can select the next sample in the sequence. The process can then be repeated until there are no further samples to be tested, or some other condition is reached.

The high-throughput system can be applied to a number of different applications, such as research or quality control/quality assurance applications. In some situations, the material to be imaged may be well homogenized prior to aspiration by the probe. In other situations, however, a dispersion step may be performed before sampling, such as with a stirrer. In one embodiment, it is contemplated that the pressure source in the probe itself could be used to mix the sample, such as by aspiring and expelling the sample repeatedly. This could allow larger contaminant particles such as flakes of plastic or stainless steel, which might otherwise sink, to be detected in quality control situations. It could also create droplets of liquid contaminants, such as silicone lubricants, that can be detected.

Where the sample is more delicate, such as in the case of complex proteins, the probe can perform a first low-flow-rate pass to image intact particles and/or aggregates, followed by a more vigorous mixing that may suspend higher density particles in the sample before a second set of images is taken. In one example, a probe moves to a sample cup and draws up a small sample (e.g., <500 μl) at low flow rate (typically <2 ml/min) and images that sample. The sample is then flushed back into the same sample cup at higher rate to agitate the sample. The sample is then again drawn into the imaging flow cell for analysis. The first images will show any protein aggregates, but probably not show higher density materials (e.g., steel or glass particles) that may have settled in the sample cup. Later images will tend to show any higher density particles. Fluid density for the formulations is expected to range from 0.997 g/ml to 1.08 g/ml with dynamic viscosity of 1 to 20 centipoise. Protein aggregate densities should range from 1 g/ml (loose aggregate) to 1.4 g/ml (tight aggregate). Particulate contaminant densities are expected to range from 0.97 g/ml (silicone oil) to 8 g/ml (stainless steel).

Systems according to the invention can be configured to handle different types of materials. On one end of the spectrum, industrial applications can provide for flow rates of 2 liters per minute or more with bypass and recirculation features. At the low end of the spectrum, a system that handles delicate proteins might operate at a non-recirculating, no-bypass flow rate of 2 milliliters per minute or less. A lower end flow rate for the recirculating flow cell (with ears for bypass flow) is probably on the order of 100 ml/minute, although more typical is greater than 1 l/minute. A lower end flow rate for a small volume (bio) flow cell (no bypass flow) is probably on the order of 100 μl/minute, with typical flow rate of 0.4-1.5 ml/minute.

Figure 11:
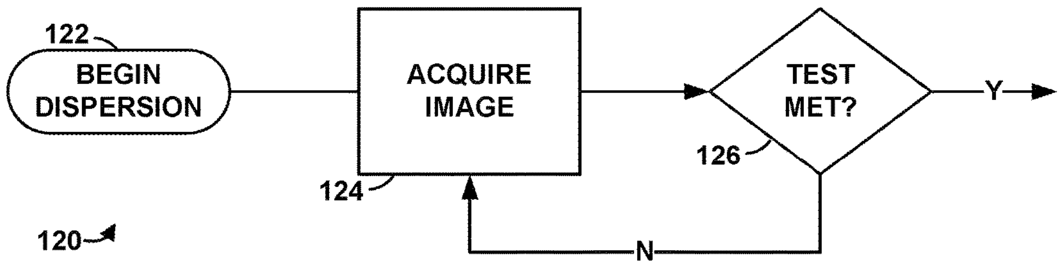
FIG. 11 is a flowchart for an illustrative sonication process according to the invention.

Referring to FIGS. 6 and 11, systems according to the invention can apply a dispersion metric to determine in real time how well the particles are dispersed using the in-line ultrasound probe 50 in a process known as sonication. More specifically, after dispersion begins, the microfluidic detection cell 20 acquires images (step 124) and repeatedly computes a value for the dispersion metric for these images (step 126) and determines whether it has stabilized by comparing it with earlier values. Reaching a stabilized dispersion metric value indicates that the particle size in the instrument has reached a steady state, such as a state where the particles are non-aggregated (primary) particles. This indication can be used to initiate measurements using the other measurement cell or to validate measurements where they are ongoing. The stabilization signal can also be used to cause sonication to be stopped or slowed.

A variety of approaches to image evaluation have been tried and some of them provide at least some information, such as an indication of makeup, uniformity, complexity, or evolution thereof, about dispersion from one or more images. But an entropy function is now preferred. Entropy is a way to measure how "busy" an image is and it may be calculated according to the following function:

$$\text{Entropy}=\Sigma_i P_i \text{ Log}_2 P_i$$

There are two methods to calculate entropy according to the above equation. $P_i$ can be a probability that the difference between two adjacent pixels is i (Cornell method). Alternatively $P_i$ can be a probability that an individual pixel value is I (Matlab method). In a general aspect therefore, the statistical function used on acquired image data to gage heterogeneity may involve calculating a measure of entropy in the plurality of acquired images. The measure of entropy of each acquired image may be calculated from a sum of probabilities of pixel values or differences between adjacent pixel values in the image being a given value.

Examples of other types of dispersion metrics can include performing image processing calculations or statistical evaluations, such as by computing means, skews, and/or standard deviations. More detailed types of analyses can also be undertaken, such as ones in which distances between nearest neighbors are calculated and/or ones in which differently sized, differently shaped, or differently shaped particles are analyzed independently. There are also different ways to test the dispersion metric, such as by testing for rates of change, thresholds, or target ranges of one or more parameters. The test may be performed to seek an end point, like in a titration, but it can also be used in other ways, such as by being added as another field in a measurement data set or by using it as a feedback parameter in a process to keep the process within acceptable limits.

Different overall approaches may have different benefits for different types of processes and samples. Continuously monitoring a quick calculation for stabilization might be of more use in a real-time industrial process environment, for example, while evaluating a more complex function for a particular end condition might be more suited to analyzing mixtures of different particle species in a research setting, such as in a situation where polydispersity or complex proteins are present. It may also be desirable in some circumstances to perform a series of experiments under different conditions, such as with different flow rates or blender speeds.

Figure 12:
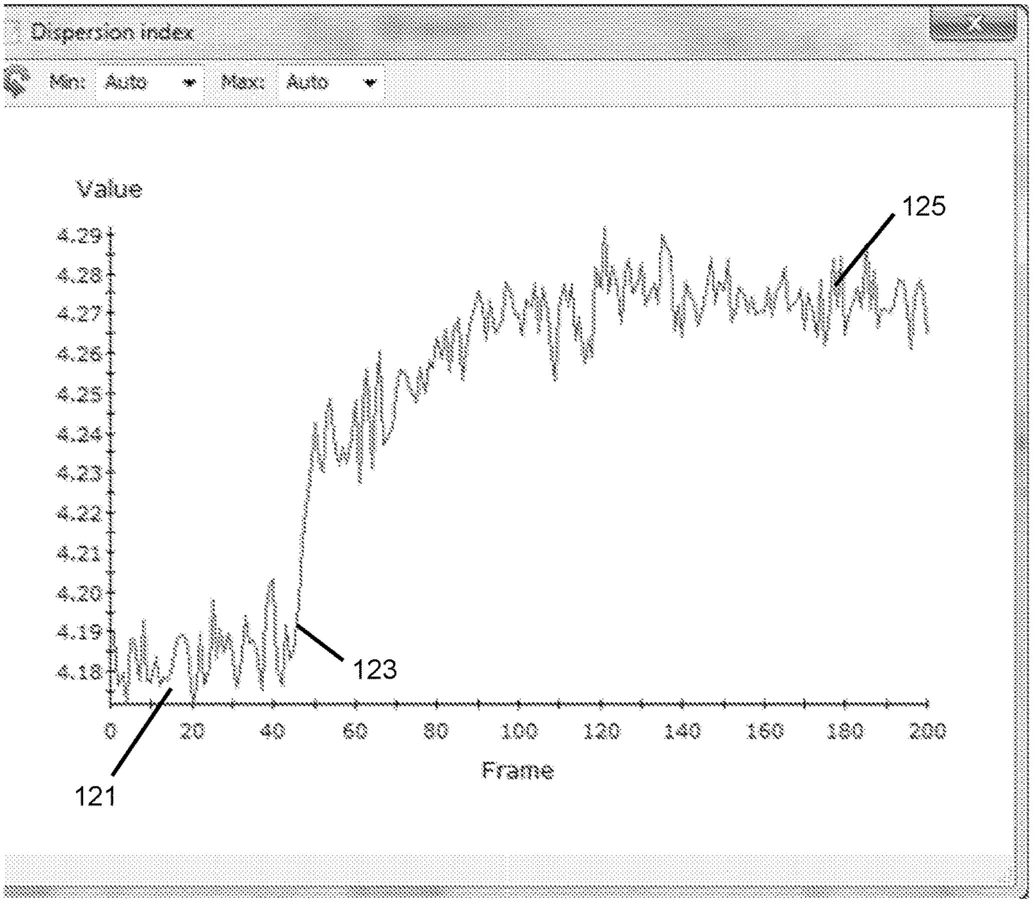
FIG. 12 is a plot of entropy against time for a sonification of carbon black experiment.
Figure 13:
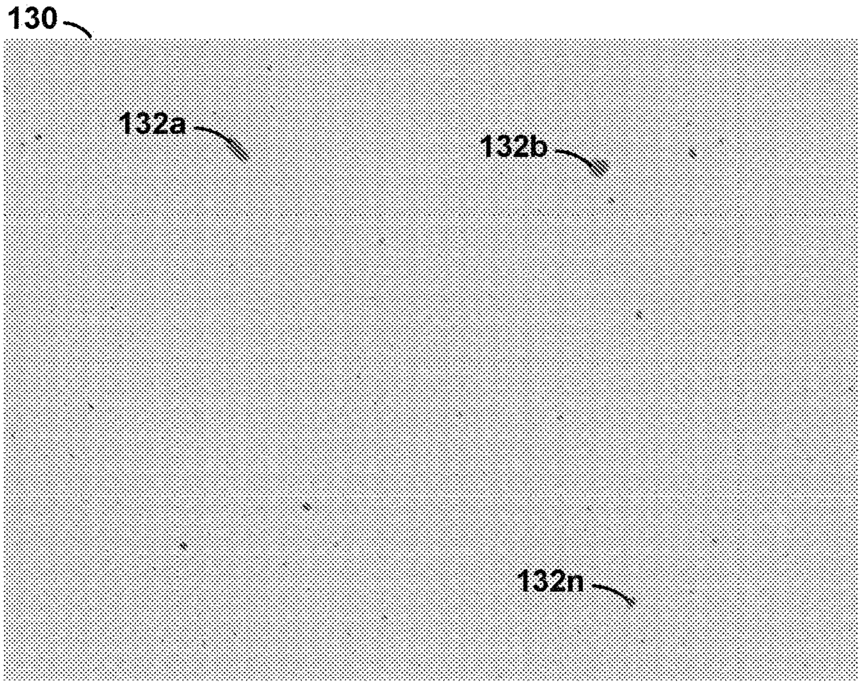
FIG. 13 is an image of a carbon black sample acquired using the microfluidic cell block of FIG. 2 in the particle characterization system of FIG. 1 at the onset of the sonication experiment.
Figure 14:
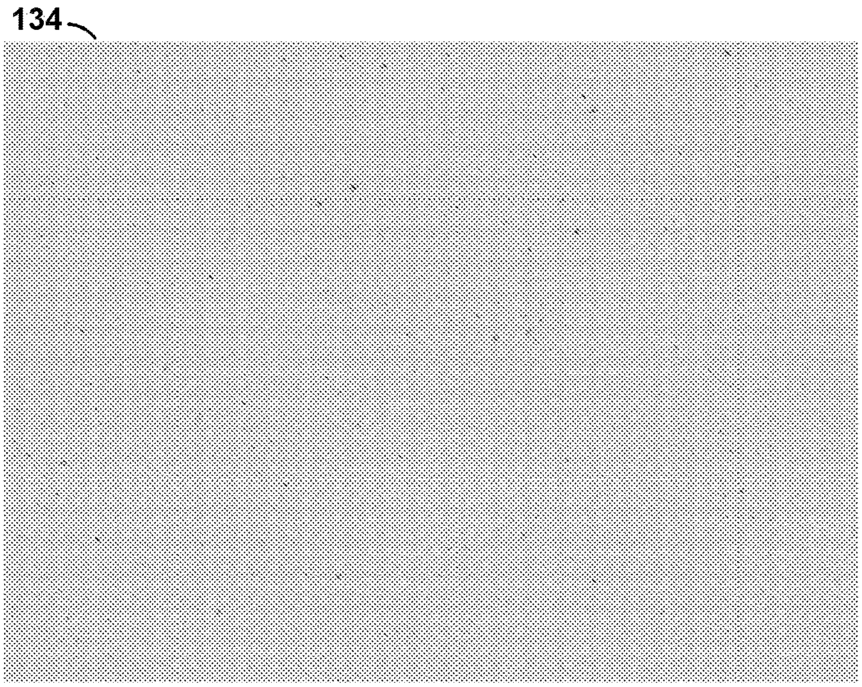
FIG. 14 is an image of a carbon black sample acquired using the microfluidic cell block of FIG. 2 in the particle characterization system of FIG. 1 at the end of the sonication experiment.

Referring also to FIGS. 12-14, a sample of carbon black was introduced in the wet dispersion process shown in FIG. 6 and a first image 130 was acquired (FIG. 13). This initial image shows that there were initially a number of significantly aggregated particles and this is reflected in the lower initial dispersion index (region 121 in FIG. 12). As sonication took place (region 123), the dispersion index rose and finally stabilized at a higher level (region 125), as shown in FIG. 12. An image taken after stabilization (FIG. 14) confirms that the aggregated particles had been broken up. In this example, the dispersion index is derived from a measure of entropy, as described above. An increase in the entropy of the acquired images therefore indicates an increase in dispersion of particles in the sample.

The present invention has now been described in connection with a number of specific embodiments thereof. However, numerous modifications which are contemplated as falling within the scope of the present invention should now be apparent to those skilled in the art. For example, while the particles are described as being suspended in a liquid in the embodiments shown, they can also be suspended in a gas, or may be suspensions of particles of a liquid in another liquid. More comprehensively, systems according to the invention are applicable to heterogeneous fluid samples that include a continuous liquid or gas phase and a discontinuous phase that can include either a liquid, solid, or gas. It is therefore intended that the scope of the present invention be limited only by the scope of the claims appended hereto. In addition, the order of presentation of the claims should not be construed to limit the scope of any particular term in the claims.

The invention claimed is:

1. A heterogeneous fluid sample characterization method, comprising:

illuminating a heterogeneous fluid sample from an in-line particle disperser;

causing the heterogeneous fluid sample to flow past a two-dimensional array detector;

acquiring at least one image of the illuminated heterogeneous fluid sample;

returning the illuminated heterogeneous fluid sample to the in-line particle disperser;

extracting a summarizing metric from the images, wherein extracting the summarizing metric comprises extracting a dispersion metric from the images;

detecting a stabilization or a rate of change of the dispersion metric;

adjusting a process that is applied to the heterogeneous fluid sample based on the dispersion metric in real time, wherein the process is one or more of a particle creation, a particle modification, a particle mixing, a sonication, or a dispersive process: and using the stabilization or rate of change of the dispersion metric to confirm that aggregated particles are not breaking up or have been broken up.

2. The method of claim 1 wherein the step of extracting a summarizing metric includes extracting information about particle size or flow.

3. The method of claim 1 wherein the step of extracting a dispersion metric from the images applies an entropy function to the images.

4. The method of claim 3 further including:

the step of reporting the detection of the stabilization or the rate of change of the dispersion metric.

5. The method of claim 1 further including the step of performing a second measurement on the heterogeneous fluid sample.

6. The method of claim 5 wherein the second measurement is a laser diffraction measurement.

7. The method of claim 6 wherein the dispersion metric is used to: trigger the second measurement in real time and/or validate the second measurement.

8. A heterogeneous fluid sample characterization method, comprising:

illuminating a heterogeneous fluid sample from an in-line particle disperser;

detecting the heterogeneous fluid sample via a two-dimensional array detector;

acquiring at least one image of the illuminated heterogeneous fluid sample;

returning the illuminated heterogeneous fluid sample to the in-line particle disperser;

extracting a summarizing metric from the images, wherein extracting the summarizing metric comprises extracting a dispersion metric from the images;

detecting a stabilization or a rate of change of the dispersion metric;

adjusting a process that is applied to the heterogeneous fluid sample based on the dispersion metric in real time, wherein the process is one or more of a particle creation, a particle modification, a particle mixing, a sonication, or a dispersive process; and using the stabilization or rate of change of the dispersion metric to confirm that aggregated particles are not breaking up or have been broken up.

9. The method of claim 8 wherein extracting a summarizing metric comprises extracting information about particle size or flow.

10. The method of claim 8 wherein extracting a dispersion metric from the images applies an entropy function to the images.

11. The method of claim 10 comprising reporting the detection of the stabilization or the rate of change of the dispersion metric.

12. The method of claim 8 comprising performing a second measurement on the heterogeneous fluid sample.

13. The method of claim 12 wherein the second measurement comprises a laser diffraction measurement.

14. The method of claim 12 wherein the dispersion metric is used to trigger the second measurement in real time and/or validate the second measurement.

15. The method of claim 3, wherein the entropy function involves calculating a measure of entropy in the images and the measure of entropy is calculated from a sum of probabilities of pixel values, or wherein the measure of entropy is calculated from a sum of probabilities of differences between adjacent pixel values.

16. The method of claim 10, wherein the entropy function involves calculating a measure of entropy in the images and the measure of entropy is calculated from a sum of probabilities of pixel values, or wherein a measure of entropy is calculated from a sum of probabilities of differences between adjacent pixel values.

* * * * *